(12) United States Patent
Sonnino et al.

(10) Patent No.: US 12,138,277 B2
(45) Date of Patent: Nov. 12, 2024

(54) OLIGOSACCHARIDES FOR USE IN THE TREATMENT OF PARKINSON'S DISEASE

(71) Applicant: UNIVERSITA' DEGLI STUDI DI MILANO, Milan (IT)

(72) Inventors: Sandro Sonnino, Milan (IT); Elena Chiricozzi, Milan (IT)

(73) Assignee: UNIVERSITA' DEGLI STUDI DI MILANO, Milan (IT)

( * ) Notice: Subject to any disclaimer, the term of this patent is extended or adjusted under 35 U.S.C. 154(b) by 756 days.

(21) Appl. No.: 17/259,446

(22) PCT Filed: Jul. 11, 2019

(86) PCT No.: PCT/IB2019/055913
§ 371 (c)(1),
(2) Date: Jan. 11, 2021

(87) PCT Pub. No.: WO2020/012400
PCT Pub. Date: Jan. 16, 2020

(65) Prior Publication Data
US 2021/0275555 A1 Sep. 9, 2021

(30) Foreign Application Priority Data
Jul. 11, 2018 (IT) .......................... 102018000007093

(51) Int. Cl.
A61K 31/702 (2006.01)
A61P 25/16 (2006.01)
A61P 25/28 (2006.01)

(52) U.S. Cl.
CPC ............ *A61K 31/702* (2013.01); *A61P 25/16* (2018.01); *A61P 25/28* (2018.01)

(58) Field of Classification Search
CPC ........ A61K 31/702; A61P 25/16; A61P 25/28; A61P 25/00; A61P 25/10
USPC .......................................................... 514/61
See application file for complete search history.

(56) References Cited

U.S. PATENT DOCUMENTS 7,842,677 B2 * 11/2010 DeFrees .................. A61P 25/16
514/61

FOREIGN PATENT DOCUMENTS

WO 00/35932 A1 6/2000
WO 2012/091606 A1 7/2012

OTHER PUBLICATIONS

Siebert et al, Chemistry: A European Journal, 2006, 12, 388-402.*
Neu et al, PNAS, 2008, 105(13), 5219-5224.*
The Merck Manual 16th Edn, 1992, pp. 1493-1494, 1403-1404, 1488-1489.*
Dugger et al, Col Spring Harb Perspect Biol, 2016, 9, 1-22.*
International Search Report and Written Opinion of the International Searching Authority for International Patent Application No. PCT/IB2019/055913 mailed Oct. 31, 2019, 9 pages.
Siebert, HC et al., "Carbohydrate chain of ganglioside GM1 as a ligand: identification of the binding strategies of three 15 mer peptides and their divergence from the binding modes of growth-regulatory galectin-1 and cholera toxin", Chemistry—A European Journal, 12(2): 388-402 (Dec. 2005).
Bronstein, J. et al., "Deep Brain Stimulation for Parkinson Disease: An Expert Consensus and Review of Key Issues", Arch Neurol., 68(2): 165-171 (Feb. 2011).
Chiricozzi, E. et al., "Role of the GM1 ganglioside oligosaccharide portion in the TrkA-dependent neurite sprouting in neuroblastoma cells", Journal of Neurochemistry, 143: 645-659 (2017).
Chiricozzi, E. et al., "GM1 promotes TrkA-mediated neuroblastoma cell differentiation by occupying a plasma membrane domain different from TrkA", Journal of Neurochemistry, 149: 231-241 (2019).
Chiricozzi, E. et al., "The Neuroprotective Role of the GM1 Oligosaccharide, II3Neu5Ac-Gg4, in Neuroblastoma Cells", Molecular Neurobiology, 1-30 (2019).
Chiricozzi, E. et al., "Parkinson's disease recovery by GM1 oligosaccharide treatment in the B4galnt1+/− mouse model", Scientific Reports, 9(19330): 1-15 (2019).
Chiricozzi, E. et al., "Turning the spotlight on the oligosaccharide chain of GM1 ganglioside", Glycoconjugate Journal, 38: 101-117 (2021).
Di Biase, E. et al., "Gangliosides in the differentiation process of primary neurons" the specific role of GM1-oligosaccharide, Glycoconjugate Journal, 1-15 (2020).
Di Biase, E. et al., "GM1 Oligosaccharide Crosses the Human Blood-Brain Barrier In Vitro by a Paracellular Route", International Journal Molecular Sciences, 21: 1-25 (2020).
Fazzari, M. et al., "The oligosaccharide portion of ganglioside GM1 regulates mitochondrial function in neuroblastoma cells", Glycoconjugate Journal, 1-14 (2020).
Ghidoni, R. et al., "On the Structure of Two New Gangliosides from Beef Brain", Journal of Neurochemistry, 27: 511-515 (1976).
Liu, Y. et al., "A genetic model of substrate deprivation therapy for a glycosphingolipid storage disorder", The Journal of Clinical Investigation, 103(4): 497-505 (1999).
Lunghi, G. et al., "Modulation of calcium signaling depends on the oligosaccharide of GM1 in Neuro2a mouse neuroblastoma cells", Glycoconjugate Journal, 37: 713-727 (2020).
Orlando, P. et al., "The Fate of Tritium Labeled GM1 Ganglioside Injected in Mice", Pharmacological Research Communications, 11(9): 759-773 (1979).
"Parkinson's Disease: National clinical guideline for diagnosis and management in primary and secondary care", The National Collaborating Centre for Chronic Conditions, Royal College of Physicians, 1-776 (2006).
Sonnino, S. et al., "Preparation of radiolabeled gangliosides", Glycobiology, 6(5): 479-487 (1996).

(Continued)

*Primary Examiner* — Ganapathy Krishnan
(74) *Attorney, Agent, or Firm* — Merchant & Gould P.C.

(57) ABSTRACT

Oligosaccharides are for use in the treatment of neurodegenerative diseases of the central nervous system, in particular Parkinson's disease, and to pharmaceutical compositions including one or more of the oligosaccharides.

4 Claims, 3 Drawing Sheets

(56) References Cited

OTHER PUBLICATIONS

Tettamanti, G. et al., "A New Procedure for the Extraction, Purification and Fractionation of Brain Gangliosides", Biochimica et Biophysica Acta, 296: 160-170 (1973).
Wu, G. et al., "Mice Lacking Major Brain Gangliosides Develop Parkinsonism", Neurochem Res, 36: 1706-1714 (2011).
Wu, G. et al., "Deficiency of Ganglioside GM1 Correlates With Parkinson's Disease in Mice and Humans", Journal of Neuroscience Research, 1-12 (2012).

* cited by examiner

A

B

*p< 0.001

OLIGOSACCHARIDES FOR USE IN THE TREATMENT OF PARKINSON'S DISEASE

This application is a National Stage Application of PCT/IB2019/055913, filed 11 Jul. 2019, which claims benefit of Patent Application Serial No. 102018000007093, filed 11 Jul. 2018 in Italy and which applications are incorporated herein by reference. To the extent appropriate, a claim of priority is made to each of the above-disclosed applications.

The present invention finds application in the medical field, and in particular for the treatment of Parkinson's disease.

BACKGROUND ART

Parkinson's disease is a neurodegenerative disease, the typical motor symptoms of which are the result of the death of the substantia nigra cells which synthesize and release dopamine.

To date, a cure for Parkinson's is not available. Pharmacological treatment, surgery and multidisciplinary management can provide relief from symptoms. The drugs mainly used in the treatment of motor symptoms are levodopa, dopamine agonists and MAO-B inhibitors (monoamine oxidase inhibitor) (The National Collaborating Center for Chronic Conditions 2006 Parkinson's Disease, London, Royal College of Physicians, 59-100).

At the stage where drugs are no longer sufficient to control symptoms, surgery and deep brain stimulation can be useful (Bronstein J M et al. 2011 Arch. Neurol. 68(2):165).

The need for a therapeutic approach capable of treating Parkinson's disease is thus strongly felt.

SUMMARY OF THE INVENTION

It has surprisingly been shown that the administration of the oligosaccharides of the present invention to a subject is able to eliminate the symptoms related to neurodegenerative diseases of the central nervous system, in particular Parkinson's disease.

OBJECT OF THE INVENTION

Figure 1:
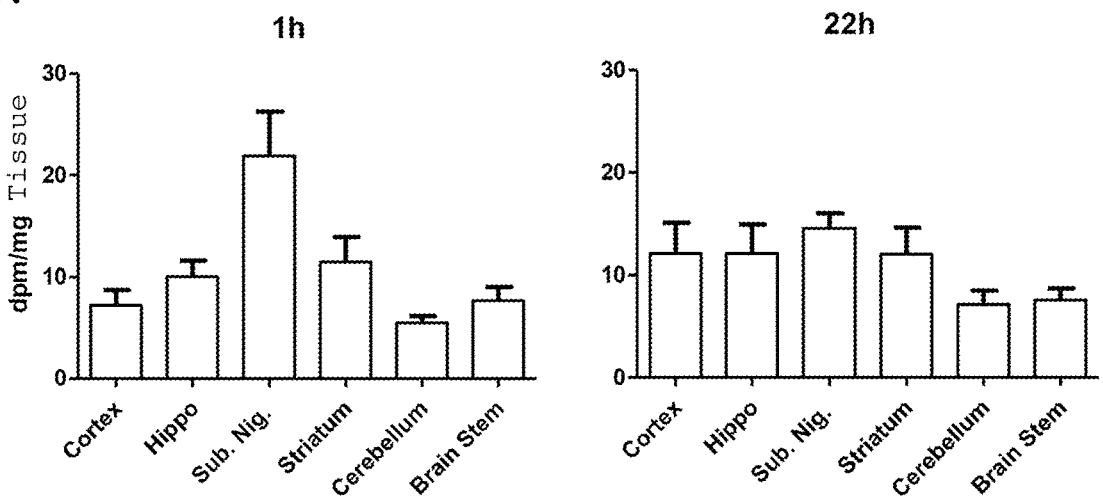
FIG. 1: Distribution of radioactivity associated with oligosaccharide β-[6-$^3$H]Gal-(1-3)-β-GalNAc-(1-4)-[α-Neu5Ac-(2-3)]-β-Gal-(1-4)-Glc following administration A) subcutaneous, B) intraperitoneal, and C) intravenously, measured at 1 hour and 22 hours after administration.
Figure 1:
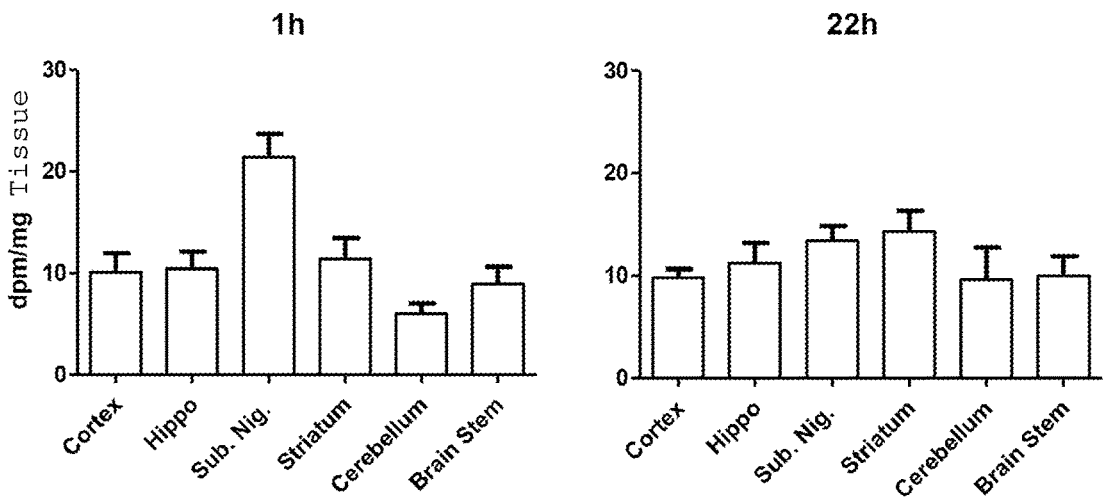
Figure 1:
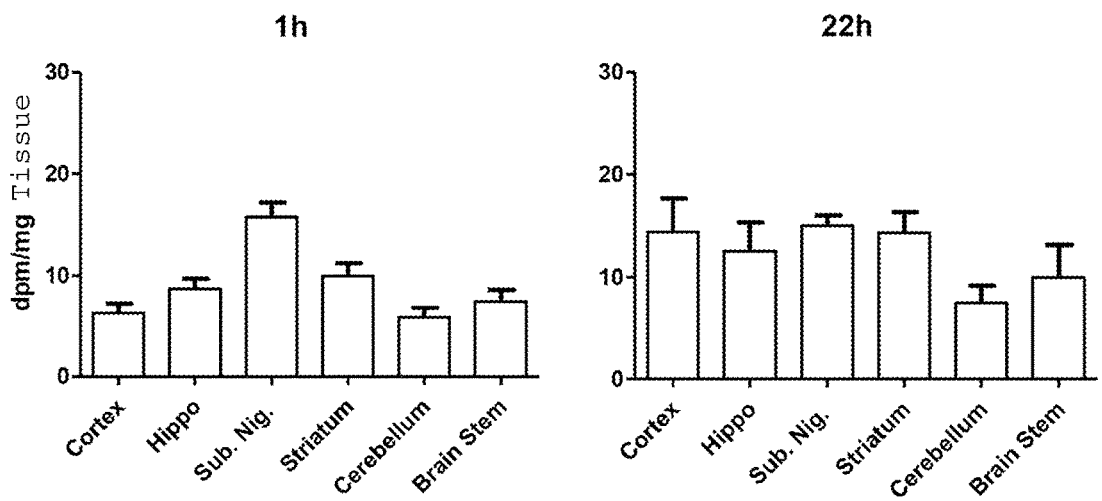

In a first object, the present invention describes compounds with oligosaccharide structure.

In a second object, pharmaceutical compositions are described comprising such oligosaccharide composites.

In a third object, the compounds of the invention are described for medical use and, in particular, for the treatment of Parkinson's disease.

In a further object it is described a method for treating Parkinson's disease comprising the administration of a pharmaceutically effective amount of a compound of the invention to a patient in need thereof.

DETAILED DESCRIPTION OF THE INVENTION

According to a first object, compounds with oligosaccharide structure are described.

In particular, such compounds have the following formula (1):

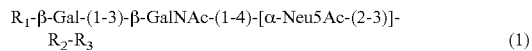

$$R_1\text{-}\beta\text{-Gal-}(1\text{-}3)\text{-}\beta\text{-GalNAc-}(1\text{-}4)\text{-}[\alpha\text{-Neu5Ac-}(2\text{-}3)]\text{-}R_2\text{-}R_3 \quad (1)$$

wherein:
$R_1$ is absent or selected from α-Fuc(1-2), α-Neu5Ac-(2-3);
$R_2$ is selected from -(1-4)-β-Gal, -(1-4)-Gal;
$R_3$ is absent or selected from (1-4)-Glc, -(1-4)-sorbitol.

For the purposes of the present invention, preferred compounds are represented by:

1. β-Gal-$_{(1-3)}$-β-GalNAc-$_{(1-4)}$-[α-Neu5Ac-$_{(2-3)}$]-β-Gal-$_{(1-4)}$-Glc,
2. β-Gal-$_{(1-3)}$-β-GalNAc-$_{(1-4)}$-[α-Neu5Ac-$_{(2-3)}$]-β-Gal-$_{(1-4)}$-sorbitol,
3. β-Gal-$_{(1-3)}$-β-GalNAc-$_{(1-4)}$-[α-Neu5Ac-$_{(2-3)}$]-β-Gal,
4. α-Fuc (1-2)-β-Gal-$_{(1-3)}$-β-GalNAc-$_{(1-4)}$ [α-Neu5Ac-$_{(2-3)}$]-β-Gal-$_{(1-4)}$-Glc,
5. α-Fuc$_{(1-2)}$-β-Gal-$_{(1-3)}$-β-GalNAc-$_{(1-4)}$-[α-Neu5Ac-$_{(2-3)}$]-β-Gal-$_{(1-4)}$-sorbitol,
6. α-Fuc$_{(1-2)}$-β-Gal-$_{(1-3)}$-β-GalNAc-$_{(1-4)}$-[α-Neu5Ac-$_{(2-3)}$]-β-Gal,
7. α-Neu5Ac-$_{(2-3)}$-β-Gal-$_{(1-3)}$-β-GalNAc-$_{(1-4)}$-[α-Neu5Ac-$_{(2-3)}$]-β-Gal$_{(1-4)}$-Glc,
8. α-Neu5Ac-$_{(2-3)}$-β-Gal-$_{(1-3)}$-β-GalNAc-$_{(1-4)}$-[α-Neu5Ac-$_{(2-3)}$]-β-Gal$_{(1-4)}$-sorbitol,
9. α-Neu5Ac-$_{(2-3)}$-β-Gal-$_{(1-3)}$-β-GalNAc-$_{(1-4)}$-[α-Neu5Ac-$_{(2-3)}$]-Gal.

Pharmaceutical compositions comprising the compounds described above represent further objects of the invention.

Said oligosaccharides are administered au such or in the form of a pharmaceutical composition in which one or more active compounds are as a mixture or mixed with one or more pharmaceutically acceptable excipients.

The pharmaceutical compositions for use according to the present invention may be formulated in a conventional manner using one or more pharmaceutically acceptable excipients including carriers, diluents and adjuvants which facilitate the processing of the active compounds in preparations which can be used physiologically.

In particular, an appropriate composition is dependent on the selected route of administration.

It has also been shown that said oligosaccharides, when administered intraperitoneally, intravenously or subcutaneously, overcome the blood-brain barrier and reach the unchanged the extracellular environment of neurons.

In a preferred embodiment, the route of administration is intraperitoneal, subcutaneous or intravenous.

According to an aspect of the present invention, the pharmaceutical compositions comprising the oligosaccharides described above may comprise one or more further active principles.

According to a third object, the compounds of the invention are described for medical use.

In a preferred embodiment, said oligosaccharides for medical use are one or more of the oligosaccharides selected from the group comprising:
1. β-Gal-$_{(1-3)}$-β-GalNAc-$_{(1-4)}$-[α-Neu5Ac-$_{(2-3)}$]-β-Gal-$_{(1-4)}$-Glc,
2. β-Gal-$_{(1-3)}$-β-GalNAc-$_{(1-4)}$-[α-Neu5Ac-$_{(2-3)}$]-β-Gal-$_{(1-4)}$-sorbitol,
3. β-Gal-$_{(1-3)}$-β-GalNAc-$_{(1-4)}$-[α-Neu5Ac-$_{(2-3)}$]-β-Gal,
4. α-Fuc$_{(1-2)}$-β-Gal-$_{(1-3)}$-β-GalNAc-$_{(1-4)}$-[α-Neu5Ac-$_{(2-3)}$]-β-Gal-$_{(1-4)}$-Glc,
5. α-Fuc(1-2)-β-Gal-$_{(1-3)}$-β-GalNAc-$_{(1-4)}$-[α-Neu5Ac-$_{(2-3)}$]-β-Gal-$_{(1-4)}$-sorbitol,
6. α-Fuc$_{(1-2)}$-β-Gal-$_{(1-3)}$-β-GalNAc-$_{(1-4)}$-[α-Neu5Ac-$_{(2-3)}$]-Gal,
7. α-Neu5Ac-$_{(2-3)}$-β-Gal-$_{(1-3)}$-β-GalNAc-$_{(1-4)}$-[α-Neu5Ac-$_{(2-3)}$]-β-Gal (1-4)-Glc,
8. α-Neu5Ac-$_{(2-3)}$-β-Gal-$_{(1-3)}$-β-GalNAc-$_{(1-4)}$-[α-Neu5Ac-$_{(2-3)}$]-β-Gal$_{(1-4)}$-sorbitol,
9. α-Neu5Ac-$_{(2-3)}$-β-Gal-$_{(1-3)}$-β-GalNAc-$_{(1-4)}$-[α-Neu5Ac-$_{(2-3)}$]-Gal.

Exposure to said oligosaccharides has shown to eliminate the motor symptoms typically associated with neurodegenerative diseases of the central nervous system, to reduce the cerebral aggregation of α-synuclein and the formation of plaques on the surface of neurons.

According to a preferred aspect of the present invention, the oligosaccharides reported above are therefore described for medical use in the treatment of neurodegenerative pathologies, wherein said pathologies are selected from the group comprising: Alzheimer's disease, Parkinson's disease, Huntington's disease, amyotrophic lateral sclerosis (ALS), progressive supranuclear palsy, frontotemporal dementia, Lewy body dementia, Creutzfeldt-Jakob disease (CJD).

In a particularly preferred aspect of the invention, said use is in the treatment of Parkinson's disease.

For the present purposes, the treatment of the pathologies is to be understood as being able to improve, and possibly eliminate, the symptoms related to the pathologies listed above.

In a particular aspect, the present invention describes the compounds listed above for medical use, where said medical use is continued for a period of 5 weeks.

In a further object it is described a method for treating neurodegenerative diseases of the central nervous system comprising the administration of a pharmaceutically effective amount of a compound of the invention to a patient in need thereof.

For the purposes of the present invention, said pathologies are selected from the group comprising: Alzheimer's disease, Parkinson's disease, Huntington's disease, amyotrophic lateral sclerosis (ALS), progressive supranuclear palsy, frontotemporal dementia, Lewy body dementia, Creutzfeldt-Jakob disease (CJD).

In a particularly preferred aspect of the invention, said disease is represented by Parkinson's disease.

In particular, the compounds of the present invention may be administered for a period of 5 weeks.

According to an aspect of the present invention, the treatment method comprising the administration of the oligosaccharides of the present invention may comprise the administration of one or more other active principles.

For the purposes of the present invention, the administration of one or more further active principles may be concurrent or within the same therapeutic protocol.

The invention will be hereinafter described with particular reference to the examples given below, which should not be understood as limiting the present invention.

Example 1

Synthesis of Oligosaccharides

The oligosaccharides of the present invention were prepared as follows:

for the oligosaccharides:
1. β-Gal-$_{(1-3)}$-β-GalNAc-$_{(1-4)}$-[α-Neu5Ac-$_{(2-3)}$]-β-Gal-$_{(1-4)}$-Glc,
4. α-Fuc$_{(1-2)}$-β-Gal-$_{(1-3)}$-β-GalNAc-$_{(1-4)}$-[α-Neu5Ac-$_{(2-3)}$]-β-Gal-$_{(1-4)}$-Glc,
7. α-Neu5Ac-$_{(2-3)}$-β-Gal-$_{(1-3)}$-β-GalNAc-$_{(1-4)}$-[α-Neu5Ac-$_{(2-3)}$]-β-Gal$_{(1-4)}$-Glc, an ozonolysis reaction was performed followed by a basic treatment with triethylamine (Ghidoni et al. 1976 J. Neurochem 27:511-515, Tettamanti et al 1973 Biochim Biophys Acta 296:160-170) from glycolipids extracted from animal tissues.

for the oligosaccharides:
2. β-Gal-$_{(1-3)}$-β-GalNAc-$_{(1-4)}$-[α-Neu5Ac-$_{(2-3)}$]-β-Gal-$_{(1-4)}$-sorbitol,
5. α-Fuc$_{(1-2)}$-β-Gal-$_{(1-3)}$-β-GalNAc-$_{(1-4)}$-[α-Neu5Ac-$_{(2-3)}$]-β-Gal-$_{(1-4)}$-sorbitol,
8. α-Neu5Ac-$_{(2-3)}$-β-Gal-$_{(1-3)}$-β-GalNAc-$_{(1-4)}$-[α-Neu5Ac-$_{(2-3)}$]-β-Gal$_{(1-4)}$-sorbitol, the synthesis started from oligosaccharides 1, 4, 7, subjected to reductive treatment with sodium borohydride, respectively.

for oligosaccharides:
3. β-Gal-$_{(1-3)}$-β-GalNAc-$_{(1-4)}$-[α-Neu5Ac-$_{(2-3)}$]-β-Gal,
6. α-Fuc$_{(1-2)}$-β-Gal-$_{(1-3)}$-β-GalNAc-$_{(1-4)}$-[α-Neu5Ac-$_{(2-3)}$]-Gal,
9. α-Neu5Ac-$_{(2-3)}$-β-Gal-$_{(1-3)}$-β-GalNAc-$_{(1-4)}$-[α-Neu5Ac-$_{(2-3)}$]-Gal.

the synthesized oligosaccharides 1, 2, 3, respectively, were subjected to a mild chemical hydrolysis.

The tritiated compounds were tritiated on the external galactose at position 6, through an enzymatic oxidation reaction with galactose oxidase followed by a reduction with sodium boron[3H]hydride (Sonnino et al. 1996 Glycobiology 6:479-487).

Example 2

Crossing of the Blood-Brain Barrier.

Wild-type mice (C57BL/6) of about 3 months were treated with β-[6-$^3$H]Gal-(1-3)-β-GalNAc-(1-4)-[α-Neu5Ac-(2-3)]-β-Gal-(1-4)-Glc.

Administration was performed intraperitoneally, subcutaneously or intravenously (Orlando P. et al 1979, Pharmacological Research Communications 11:759-773). For the intravenous route, the injection was performed in the central vein of the tail. The treatment was carried out with 10 μg of tritiated oligosaccharide (10 μCi) dissolved in 0.1 ml of saline. For each experimental group 5 animals were used. 1 hour and 22 hours after administration, the animals were sacrificed by cardiac perfusion (10 min), in order to remove the blood, especially in the central nervous system. The brain was removed and the different areas (cortex, hippocampus, substantia nigra, cerebellum, trunk) were identified and separated. Tissue samples were lyophilized, homogenized and the relative associated radioactivity was detected at the β-counter (Orlando et al 1979, Pharmacological Research Communication 11:759-773).

FIG. 1 shows the results obtained.

It is noted that a fair amount of the oligosaccharide is able to reach the central nervous system, including the substantia nigra, within a few hours from the administration.

Example 3

Symptom Recovery

A widely used animal model of PD, heterozygous mice, was used due to lack of the enzyme galactosaminyltransferase B4galnt1 (GalNacT) (Liu Y. et al 1999, J. of Clinical Investigation 103:497-505; Wu G. et al 2012, J of Neurosci Research 90:1997-2008). The B4galnt1+/−model has a reduced content of the acid Gg4 series oligosaccharides, also known as series 1, linked to the ceramide portion inserted in the plasma membrane. The chains β-Gal-(1-3)-β-GalNAc-(1-4)-[α-Neu5Ac-(2-3)]-β-Gal-(1-4)-β-Glc and α-Neu5Ac-(2-3)-β-Gal-(1-3)-β-GalNAc-(1-4)-[α-Neu5Ac-(2-3)]-β-Gal-(1-4)-β-Glc are particularly reduced in quantity. The absence of these oligosaccharides induces an accumulation of α-synuclein aggregates, especially at the level of the substantia nigra, muscle weakness and tremor (Wu G. et al 2012, J of Neurosci Research 90:1997-2008). This animal model is representative of sporadic Parkinson's disease (Wu G. et al 2012, J of Neurosci Research 90:1997-2008).

The animals were treated daily by subcutaneous, intraperitoneal or intravenous route, with an oligosaccharide selected from:
1. β-Gal-(1-3)-β-GalNAc-(1-4)-[α-Neu5Ac-(2-3)]-β-Gal-(1-4)-Glc,
2. α-Fuc (1-2)-β-Gal-(1-3)-β-GalNAc-(1-4)-[α-Neu5Ac-(2-3)]-β-Gal-(1-4)-Glc,
3. α-Neu5Ac-(2-3)-β-Gal-(1-3)-β-GalNAc-(1-4)-[α-Neu5Ac-(2-3)]-β-Gal(1-4)-Glc
4. β-Gal-(1-3)-β-GalNAc-(1-4)-[α-Neu5Ac-(2-3)]-β-Gal-(1-4)-sorbitol,
5. α-Fuc (1-2)-β-Gal-(1-3)-β-GalNAc-(1-4)-[α-Neu5Ac-(2-3)]-β-Gal-(1-4)-sorbitol
6. α-Neu5Ac-(2-3)-β-Gal-(1-3)-β-GalNAc-(1-4)-[α-Neu5Ac-(2-3)]-β-Gal(1-4)-sorbitol
7. β-Gal-(1-3)-β-GalNAc-(1-4)-[α-Neu5Ac-(2-3)]-β-Gal,
8. α-Fuc (1-2)-β-Gal-(1-3)-β-GalNAc-(1-4)-[α-Neu5Ac-(2-3)]-Gal,
9. α-Neu5Ac-(2-3)-β-Gal-(1-3)-β-GalNAc-(1-4)-[α-Neu5Ac-(2-3)]-Gal The treatment was continued for 5 weeks at a fixed dose (20 mg/kg body weight) in saline.

B4galnt1+/−control mice received saline injections. As a positive control, wild-type mice of about 3 months treated with saline were used. For each experimental group 8 mice were used. The mice were subdivided by applying the principle of randomization in the different experimental groups.

For the entire treatment period, the animals were analyzed for their behavior.

Figure 2:
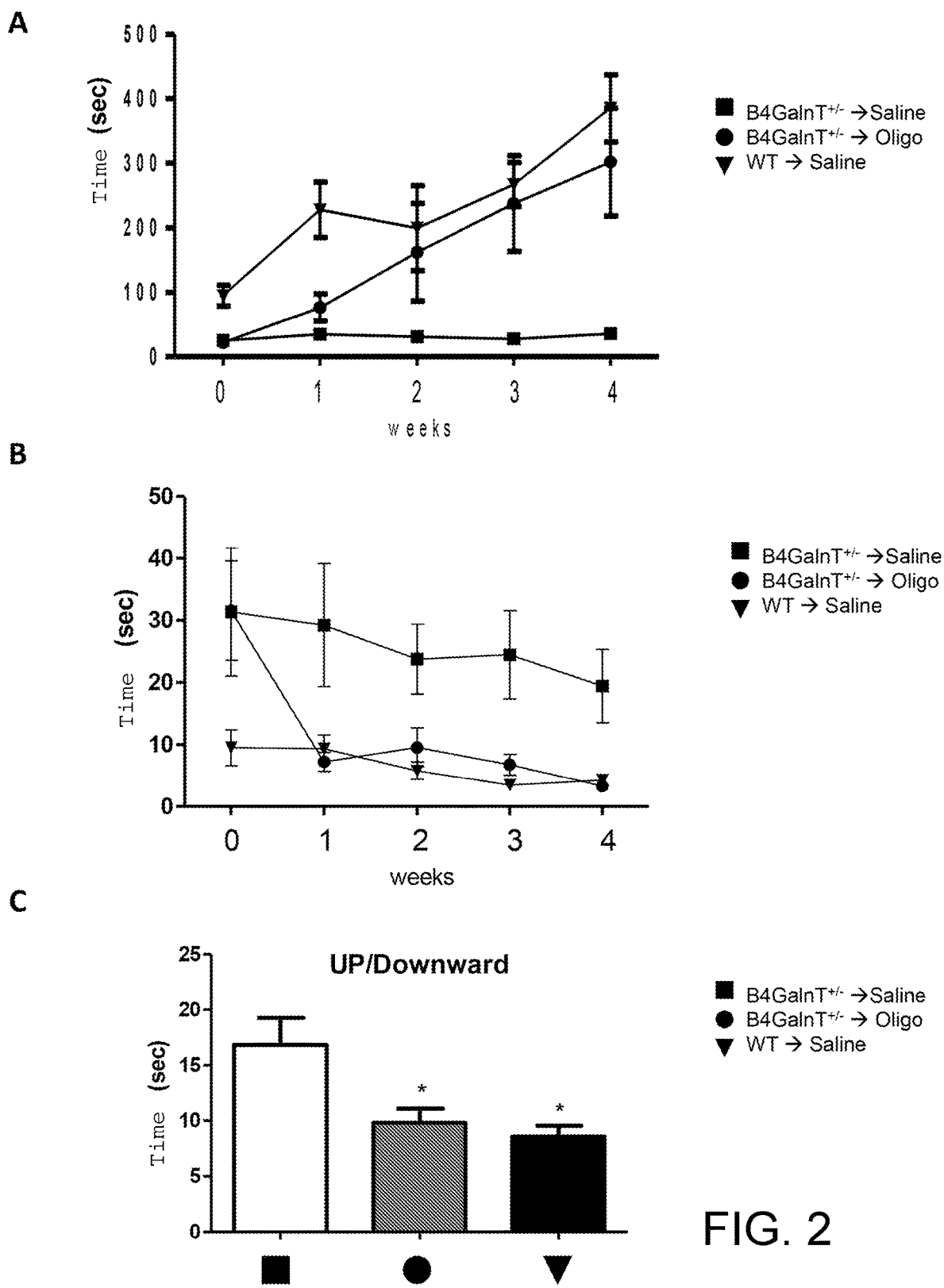
FIG. 2: Results of behavioral tests performed after intraperitoneal administration of the oligosaccharide β-Gal-(1-3)-β-GalNAc-(1-4)-[α-Neu5Ac-(2-3)]-β-Gal-(1-4)-Glc: A) Grip Test, B) Irritant Removal test, and C) Pole Test.

The behavioral tests performed were the Grip test and the Irritant Removal test, behavioral tests widely used to define the improvement capabilities of Parkinsonian mice (Wu G. et al 2012 J of Neurosci Research 90:1997-2008). One week after the start of treatment, Parkinsonian mice treated with one of the 9 oligosaccharides showed the same characteristics as the WT mice, which characteristics are maintained throughout the treatment. By way of example, FIGS. 2A and 2B show the results obtained by treating with β-Gal-(1-3)-β-GalNAc-(1-4)-[α-Neu5Ac-(2-3)]-β-Gal-(1-4)-Glc. Treatment with any of the other compounds led to comparable results. At the end of the treatment, a third behavioral test was performed, Pole test, which confirmed at phenotypic level the reversion of the parkinsonian syndrome in mice treated with one of the 9 oligosaccharides. FIG. 2C show the results obtained after treating with β-Gal-(1-3)-β-GalNAc-(1-4)-[α-Neu5Ac-(2-3)]-β-Gal-(1-4)-Glc.

At the end of the treatment, the mice were sacrificed by cardiac perfusion with saline and biochemical investigations were conducted to verify the impact of the treatment on the accumulation of α-synuclein at the level of the substantia nigra.

For each experimental group, the mice were divided into 2 subgroups: 4 mice were used for IHC investigations and 4 mice for IB investigations (Wu et al. 2011 Neurochem Research 36:1706-1714; Wu G. et al 2012 J of Neurosci Research 90:1997-2008).

The 4 brains destined for IHC were fixated overnight in a 4% paraformaldehyde solution and subsequently transferred in a 30% sucrose solution for cryoprotection and stored at 4° C.

Coronal sections (20 μm) were treated with primary anti-α-syn antibody (mouse, 1:2000 BD Science) and secondary anti-mouse antibody (alexa fluor 568, thermofisher).

The 4 brains intended for IB investigations were divided into substantia nigra, hippocampus and striatum. The tissues were homogenized and lysed. 20 μg of protein were separated by SDS-page using precasted gel (4-20% polyacrylamide, Biorad) and transferred to PVDF membranes. The presence of α-synuclein oligomers was performed using primary anti-α-syn antibody (mouse, 1:1000 BD Science) and secondary anti-mouse antibody (1:2000, thermofisher).

Experiments revealed a significant decrease in α-synuclein levels in treated mice compared to controls (data not shown).

Example 4

Activation of Protein Synthesis Involved in the Protection from Oxidative Stress, Excitotoxicity and Neuroinflammation.

Neuroblastoma cells of murine origin were treated with β-Gal-(1-3)-β-GalNAc-(1-4)-[α-Neu5Ac-(2-3)]-β-Gal-(1-4)-Glc to induce neuronal differentiation (Chiricozzi et al. 2017 Journal of Neurochemistry 143:645-659). After 24 h of treatment, the cells were collected for protein analysis. Proteomic analysis using mass spectroscopy revealed that treatment with β-Gal-(1-3)-β-GalNAc-(1-4)-[α-Neu5Ac-(2-3)]-β-Gal-(1-4)-Glc is able to induce the expression of 320 proteins. These proteins are involved in cellular signaling of i) excitotoxicity neuroprotection; ii) inhibition of oxidative stress; iii) inhibition of microglia hyperactivation and downregulation of proinflammatory molecules.

Example 5

Excitotoxicity Protection

Figure 3:
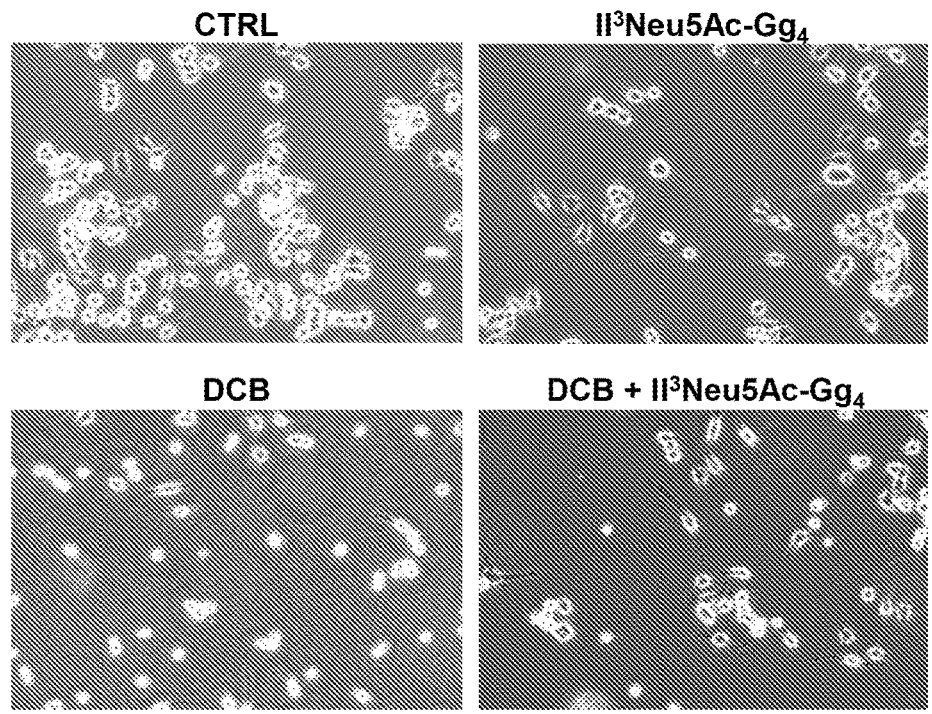
FIG. 3: A) Microscope photo representative of neuroblastoma cells treated with DCB (3',4'-Dichlorobenzamyl hydrochloride) or control, in the presence or absence of the indicated oligosaccharide. B) Live cell counts.
Figure 3:
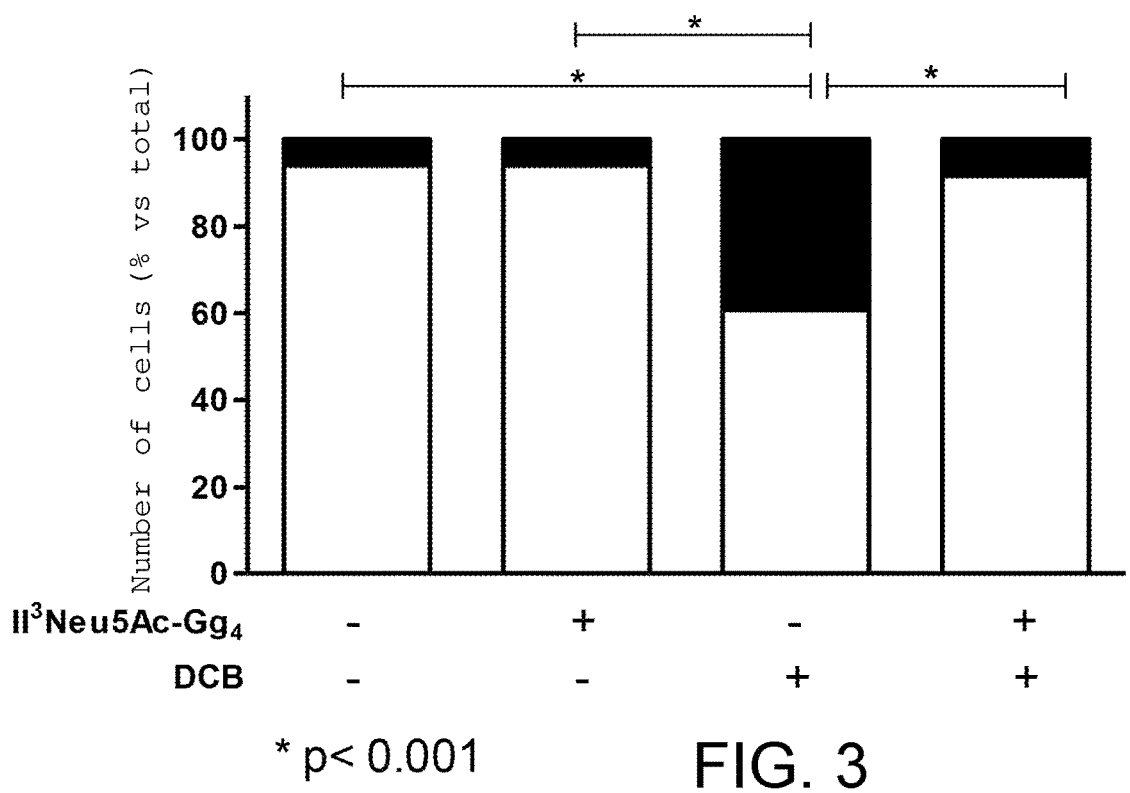

In Parkinson's disease, and more generally in the degenerative diseases of the central nervous system, there is a strong activation of the immune system, oxidative stress and excitotoxicity. Neuroblastoma cells were then treated with DCB (3',4'-Dichlorobenzamyl hydrochloride) to induce an accumulation of intracellular calcium, an experimental strategy which mimics glutamate-induced excitotoxicity. It has been shown that the administration of β-Gal-(1-3)-β-GalNAc-(1-4)-[α-Neu5Ac-(2-3)]-β-Gal-(1-4)-Glc is able to protect cells from DCB-induced death, without being toxic to cells, as shown in FIGS. 3A and 3B. In particular, the result of FIG. 3B shows an almost total recovery of cell viability from the toxicity induced by DCB.

The invention claimed is:

1. A method for the treatment of neurodegenerative diseases of the central nervous system comprising:
administering to a patient in need thereof a pharmaceutically effective amount of an one or more oligosaccharides of formula (1):

$$R_1\text{-}\beta\text{-Gal-}(1\text{-}3)\text{-}\beta\text{-GalNAc-}(1\text{-}4)\text{-}[\alpha\text{-Neu5Ac-}(2\text{-}3)]\text{-}R_2\text{-}R_3 \quad (1)$$

where $R_1$ is absent or selected from $\alpha$-Fuc(1-2), $\alpha$-Neu5Ac-(2-3);
$R_2$ is selected from -(1-4)-$\beta$-Gal if the oligosaccharide ends with a glucose, or -(1-4)-Gal if the oligosaccharide ends with a galactose;
$R_3$ is absent or selected from (1-4)-Glc, -(1-4)-sorbitol;
wherein said disease is selected from the group consisting of: Alzheimer's disease, Parkinson's disease, Huntington's disease, amyotrophic lateral sclerosis (ALS), progressive supranuclear palsy, frontotemporal dementia, Lewy body dementia, Creutzfeldt-Jakob disease (CJD).

2. The method for the treatment of neurodegenerative diseases of the central nervous system according to claim 1, wherein said oligosaccharides are selected from the group consisting of:

$\beta\text{-Gal-}_{(1\text{-}3)}\text{-}\beta\text{-GalNAc-}_{(1\text{-}4)}\text{-}[\alpha\text{-Neu5Ac-}_{(2\text{-}3)}]\text{-}(\beta\text{-Gal-}_{(1\text{-}4)}\text{-Glc}$, $\beta\text{-Gal-}_{(1\text{-}3)}\text{-}\beta\text{-GalNAc-}_{(1\text{-}4)}\text{-}[\alpha\text{-Neu5Ac-}_{(2\text{-}3)}]\text{-}(\beta\text{-Gal-}_{(1\text{-}4)}\text{-sorbitol}$, $\beta\text{-Gal-}_{(1\text{-}3)}\text{-}\beta\text{-GalNAc-}_{(1\text{-}4)}\text{-}[\alpha\text{-Neu5Ac-}_{(2\text{-}3)}]\text{-}(\beta\text{-Gal}$, $\alpha\text{-Fuc}_{(1\text{-}2)}\text{-}\beta\text{-Gal-}_{(1\text{-}3)}\text{-}\beta\text{-GalNAc-}_{(1\text{-}4)}\text{-}[\alpha\text{-Neu5Ac-}_{(2\text{-}3)}]\text{-}\beta\text{-Gal-}_{(1\text{-}4)}\text{-Glc}$, $\alpha\text{-Fuc}_{(1\text{-}2)}\text{-}\beta\text{-Gal-}_{(1\text{-}3)}\text{-}\beta\text{-GalNAc-}_{(1\text{-}4)}\text{-}[\alpha\text{-Neu5Ac-}_{(2\text{-}3)}]\text{-}\beta\text{-Gal-}_{(1\text{-}4)}\text{-sorbitol}$, $\alpha\text{-Fuc}_{(1\text{-}2)}\text{-}\beta\text{-Gal-}_{(1\text{-}3)}\text{-}\beta\text{-GalNAc-}_{(1\text{-}4)}\text{-}[\alpha\text{-Neu5Ac-}_{(2\text{-}3)}]\text{-Gal}$, $\alpha\text{-Neu5Ac-}_{(2\text{-}3)}\text{-}\beta\text{-Gal-}_{(1\text{-}3)}\text{-}\beta\text{-GalNAc-}_{(1\text{-}4)}\text{-}[\alpha\text{-Neu5Ac-}_{(2\text{-}3)}]\text{-}\beta\text{-Gal}(1\text{-}4)\text{-Glc}$, $\alpha\text{-Neu5Ac-}_{(2\text{-}3)}\text{-}\beta\text{-Gal-}_{(1\text{-}3)}\text{-}\beta\text{-GalNAc-}_{(1\text{-}4)}\text{-}[\alpha\text{-Neu5Ac-}_{(2\text{-}3)}]\text{-}\beta\text{-Gal}(1\text{-}4)\text{-sorbitol}$, and $\alpha\text{-Neu5Ac-}_{(2\text{-}3)}\text{-}\beta\text{-Gal-}_{(1\text{-}3)}\text{-}\beta\text{-GalNAc-}_{(1\text{-}4)}\text{-}[\alpha\text{-Neu5Ac-}_{(2\text{-}3)}]\text{-Gal}$.

3. The method for the treatment of neurodegenerative diseases of the central nervous system according to claim 1, comprising administering said composition intraperitoneally, subcutaneously or intravenously.

4. The method for the treatment of neurodegenerative diseases of the central nervous system according to claim 1, wherein said treatment is continued for about 5 weeks.

* * * * *